United States Patent [19]

Casutt et al.

[11] Patent Number: 5,250,699
[45] Date of Patent: Oct. 5, 1993

[54] 2-OXO-5-MERCAPTOMETHYLIMIDAZOLI-DIN-4-OLS

[75] Inventors: Michael Casutt, Erzhausen; Eike Poetsch, Mühtal, both of Fed. Rep. of Germany; Willem N. Speckamp, EC Heiloo, Netherlands

[73] Assignee: Merck Patent Gesellschaft mit Beschrankter Haftung, Darmstadt, Fed. Rep. of Germany

[21] Appl. No.: 671,770

[22] PCT Filed: Jul. 28, 1990

[86] PCT No.: PCT/EP90/01235
§ 371 Date: Apr. 10, 1991
§ 102(e) Date: Apr. 10, 1991

[87] PCT Pub. No.: WO91/02734
PCT Pub. Date: Mar. 7, 1991

[30] Foreign Application Priority Data

Aug. 12, 1989 [DE] Fed. Rep. of Germany ....... 3926690

[51] Int. Cl.$^5$ ................. C07D 233/02; C07D 233/04; C07D 233/20; C07D 233/50; C07D 233/48; C07D 233/52
[52] U.S. Cl. ................. 548/319.1; 548/110; 548/318.1
[58] Field of Search ..... 548/308, 110, 319.1, 548/318.1

[56] References Cited

U.S. PATENT DOCUMENTS 4,713,390 12/1987 Dumont et al. .................. 548/319.1

FOREIGN PATENT DOCUMENTS 0094776 11/1983 European Pat. Off. ......... 548/319.1
0242686 10/1987 European Pat. Off. ......... 548/319.1

OTHER PUBLICATIONS

Corey et al, Tetrahedron Letters, vol. 29(1), pp. 57-60 (1988).
Kazarinoff et al, J. of Biological Chem., vol. 247(1), pp. 75-83 (1972).

*Primary Examiner*—Floyd D. Higel
*Attorney, Agent, or Firm*—Millen, White, Zelano, & Branigan

[57] ABSTRACT

The invention relates to a process for the preparation of D-(+)-biotin, from a cysteine hydantoin of the formula I

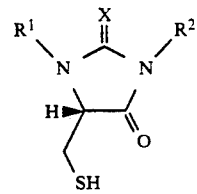

in which
$R^1$ is H, or a group $R^3R^4CH-$ or $SiR^5R^6R^7$, in which
$R^3$ and $R^4$ in each case independently of one another are H, unsubstituted or substituted alkyl, cycloalkyl, aryl, aralkyl or heteroaryl or, taken together, are unsubstituted or substituted alkylene or heteroalkylene,
$R^5$, $R^6$ and $R^7$ in each case independently of one another are unsubstituted or substituted alkyl, cycloalkyl, aryl, aralkyl or heteroaryl,
$R^2$ is H or a protective group suitable for a nitrogen atom and
X is O, S or N—$R^8$, in which
$R^8$ is an alkyl, cycloalkyl, aryl or alkoxycarbonyl group or a dialkylamino group and to intermediates which are passed through in this process.

8 Claims, No Drawings

2-OXO-5-MERCAPTOMETHYLIMIDAZOLIDIN-4-OLS

The invention relates to a process for the preparation of D-(+)-biotin from a cysteine hydantoin of the formula I

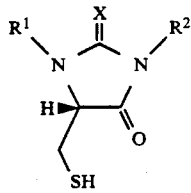

in which
R¹ is H, or a group R³R⁴CH— or SiR⁵R⁶R⁷, in which
  R³ and R⁴ in each case independently of one another are H, unsubstituted or substituted alkyl, cycloalkyl, aryl, aralkyl or heteroaryl or, taken together, are unsubstituted or substituted alkylene or heteroalkylene,
  R⁵, R⁶ and R⁷ in each case independently of one another are unsubstituted or substituted alkyl, cycloalkyl, aryl, aralkyl or heteroaryl,
R² is H or a protective group suitable for a nitrogen atom and
X is O, S or N—R⁸, in which R⁸ is an alkyl, cycloalkyl, aryl or alkoxycarbonyl group or a dialkylamino group.

The invention was based on the object of providing a novel process for the preparation of optically active D-(+)-biotin, which avoids carrying out a racemate cleavage and thus discarding or feeding back the undesired enantiomer.

Processes for the stereospecific synthesis of D-(+)-biotin from sugars of suitable configuration are known. Thus, in Tetrahedron Letters No. 32, pp. 2765-2766 (1975), D-mannose is used as a starting material, in Agric. Biol. Chem. No. 42, p. 465 (1978), D-glucose is used as a starting material and in DE-OS 3,122,562 and DE-OS 3,320,140, D-arabinose is used as a chiral starting material.

However, all these processes are characterized by a high number of synthesis steps with a consequently low total yield. The intermediates, usually uncrystallizable owing to their sugar nature, are often only obtained in unsatisfactory purity and require, owing to their polyfunctionality and the chemical lability associated therewith, the maintenance of comparatively narrow reaction parameters. A number of sugars are also inaccessible from natural sources, which results in a high price.

The use of L-cysteine, as known from U.S. Pat. Nos. 4,009,172, 4,130,713, 4,337,345 and Journal of the American Chemical Society No. 99, p. 7020 (1977), does avoid the handling of labile intermediates, but leads over a total of 18 reaction steps and with separation of undesired isomers to optically active D-(+)-biotin only in an unsatisfactory yield.

A very elegant synthesis of D-(+)-biotin from cysteine or cystine via an optically active bicyclic hydantoin derivative as an intermediate was described by E. Poetsch and M. Casutt (Chimia, 41, 148 (1987) and EP-A2-0,242,686/EP-A2-0,243,734).

The only disadvantage of this tolan synthesis is that a cyano group has to be introduced into an intermediate and the reaction thus has to be carried out using highly toxic alkali metal cyanide or trimethylsilyl cyanide.

The total synthesis of D-(+)-biotin from the hydantoin of L-cystine described by Corey et al. (Tetrahedron Letters 29, 57 (1988)) gives only a 12% yield of D-(+)-biotin over many synthesis steps and is thus unsuitable for carrying out industrially.

In a further process, substituted 3H,5H-imidazo[1,5-c]tetrahydrothiazoles are described in Journal of the American Chemical Society No. 105, p. 5946 (1983) and in EP-OS 0,094,776, from which optionally active biotin is obtained after racemate cleavage.

As the comparatively high number of steps (lacuna) associated with moderate yields in some cases and the necessity of an optical separation, even these starting materials can appear as not very suitable for the preparation of D-(+)-biotin, and there was furthermore a need for a suitable process for the simple, economic and stereospecific preparation of D-(+)-biotin.

It has now surprisingly been found that D-(+)-biotin is obtainable without additional racemate cleavage from chiral (4R/S, 5R)-5-mercaptomethylimidazolidin-4-ol of the formula II. This can be prepared from the naturally occurring amino acids L-cystine or L-cystine via a cysteine hydantoin of the formula I.

The invention therefore relates to a process for the preparation of D-(+)-biotin, characterized in that a cysteine hydantoin of the formula I

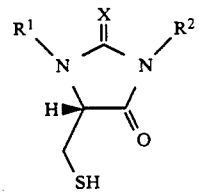

in which
R¹ is H, or a group R³R³CH— or SiR⁵R⁶R⁷, in which
  R³ and R⁴ in each independently of one another are H, unsubstituted or substituted alkyl, cycloalkyl, aryl, aralkyl or heteroaryl or, taken together, are unsubstituted or substituted alkylene or heteroalkylene,
  R⁵, R⁶ and R⁷ in each case independently of one another are unsubstituted or substituted alkyl, cycloalkyl, aryl, aralkyl or heteroaryl,
R² is H or a protective group suitable for a nitrogen atom and
X is O, S or N—R⁸, in which R⁸ is an alkyl, cycloalkyl, aryl or alkoxycarbonyl group or a dialkylamino group,
is reduced by the action of a complex reducing agent to an alcohol of the formula II

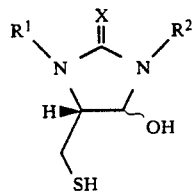

in which R¹, R² and X have the meaning indicated, this alcohol is reacted with an electrophile of the formula III

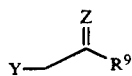

in which

Z is O, S, a dialkoxy, alkylenedioxydiyl or alkylenedithiodiyl group or N—R', in which R' is an alkyl, cycloalkyl, aryl or alkoxycarbonyl group or a dialkylamino group, Y is Cl, Br, I or —O—SO$_2$—R", in which R", is methyl, toluyl or perfluoroalkyl, and R$^9$ is alkyl or alkenyl having up to 8 C atoms, C$_6$H$_5$, —(CH$_2$)$_n$—CN, —(CH$_2$)$_n$COOR or —(CH$_2$)$_n$—OR, in which R is lower alkyl, cycloalkyl or aryl, and n is 2, 3, 4, 5, 6, 7 or 8, in the presence of a base, the alkylation product thus obtained of the formula IV

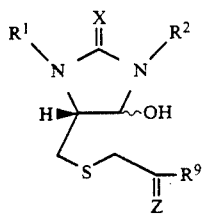

in which R$^1$, R$^2$, R$^9$, Z and X have the meaning indicated, if appropriate after etherification to give an ether of the formula IVa,

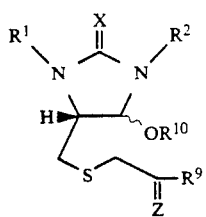

in which R$^1$, R$^2$, R$^9$, Z and X have the meaning indicated and R$^{10}$ is alkyl having 1–6 C atoms or a trialkylsilyl group, is cyclized by means of a Lewis acid, after conversion into a silyl enol ether using a silylating reagent in the presence of a base, to give a biotin derivative of the formula V

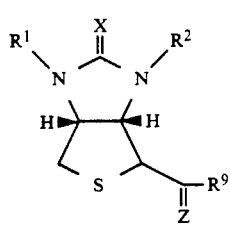

in which R$^1$, R$^2$, R$^9$ and X have the meaning indicated, and this derivative is reacted by reduction with a complex reducing agent and subsequent elimination to give a dehydrobiotin derivative of the formula VI

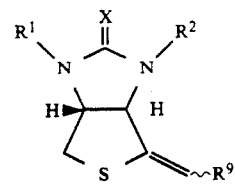

in which R$^1$, R$^2$, R$^9$ and X have the meaning indicated, which is converted into D-(+)-biotin by methods known per se.

The invention furthermore relates to a process of this type in which, for the preparation of the cysteine hydantoin of the formula I, the optically active bicyclic hydantoin of the formula VII

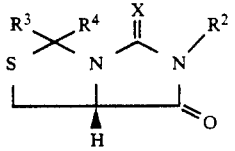

in which R$^2$, R$^3$, R$^4$ and X have the meaning indicated, is cleaved using an acid and/or a reducing agent.

The intermediate of the formulae II, IV, IVa and V passed through in the process according to the invention are novel. The invention likewise relates to the novel intermediates, namely the compounds of the formula II

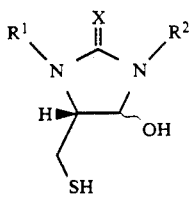

in which R$^1$, R$^2$ and X have the meaning indicated in claim 1, in particular in which R$^1$ and R$^2$ are benzyl, the compounds of the formula IV,

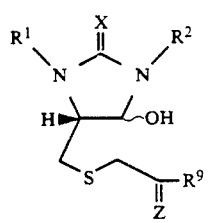

in which R$^1$, R$^2$, R$^9$, Z and X have the meaning indicated, in particular in which R$^1$ and R$^2$ are benzyl, Z is O and R$^9$ is —(CH$_2$)$_3$—COOR, in which R is lower alkyl, the compounds of the formula IVa

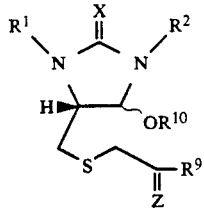

IVa in which $R^1$, $R^2$, $R^9$, $R^{10}$, Z and X have the meaning indicated, in particular in which $R^1$ and $R^2$ are benzyl, Z is O and $R^9$ is $-(CH_2)_3-COOR$, in which R is lower alkyl, and the compounds (lacuna) formula V

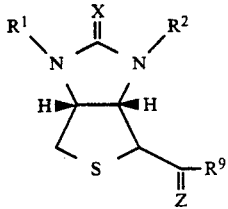

V in which $R^1$, $R^2$, $R^9$, Z and X have the meaning indicated, in particular in which $R^1$ and $R^2$ are benzyl, Z is O, and $R^9$ is $-(CH_2)_3-COOR$, in which R is lower alkyl.

The starting compounds of the formula I are prepared by methods known per se, such as are described in the literature (for example in standard works such as Houben-Weyl, Methoden der Organischen Chemie [Methods of Organic Chemistry], Georg-Thieme-Verlag, Stuttgart), in particular under reaction conditions such as are known and are suitable for said reactions. Use can also be made in this connection of variants which are known per se but which are not mentioned here in more detail.

The starting materials can be obtained, for example, according to E. J. Corey et al. (Tetrahedron Letters 29, 57 (1988)) from L-cystine or from the bicyclic hydantoin of the formula VII by cleavage using an acid and/or a reducing agent. The bicyclic hydantoins of the formula VII are known or can be prepared from L-cysteine or L-serine (EP-A2-0,243,734) by known methods.

Acids such as hydrochloric acid or sulfuric acid, for example, are suitable for the cleavage of the bicyclic compounds of the formula VII which, expediently in a solvent, for example water or alcohols, lead to the hydantoins of the formula Ia in which $R^1$=H.

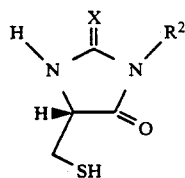

Ia

Additionally utilizable as cleavage reagent are heavy metal salts such as silver nitrate, mercury(II) chloride or mercury(II) acetate. The subsequent decomposition of the intermediately formed metal mercaptides is expediently carried out using hydrogen sulfide. Solvents suitable for this cleavage reaction are found, for example, among the alcohols such as methanol or ethanol, amides we (sic) dimethylformamide or ethers we (sic) tetrahydrofuran.

Bicyclic hydantoins of the formula VII can be reacted with reducing agents to give intermediates of the formula I in which $R^1$ is $CHR^3R^4$. Suitable reducing agents are, for example, metals such as zinc. The cleavage of the acid derivatives by reduction with metals is preferably carried out in acidic medium. Acids suitable for this purpose are, for example, mineral acids such as hydrochloric acid or sulfuric acid or organic acids such as formic acid or acetic acid. These acids are expediently used as solvents or in a mixture with other solvents such as, for example, alcohols. The reaction temperature is customarily between 0° C. and 200° C., preferably between 20° C. and 150° C. At these temperatures, the reactions are as a rule complete after 15 minutes to 24 hours.

The alcohols of the formula II can be obtained from the cysteine hydantoins of the formula I by the action of a complex reducing agent. Preferred complex reducing agents are, for example, boranes such as diborane, sodium borohydride, lithium cyanoborohydride, lithium, sodium or potassium triethylborohydride, metal hydrides such as sodium hydride or aluminum hydride, silicon hydrides such as triethylsilane, tributyltin hydride and mixed hydrides such as lithium aluminohydride, sodium aluminohydride, sodium bis-(2-methoxyethoxy)aluminum hydride, potassium borohydride or lithium borohydride, in particular diisobutylaluminum hydride (DIBAH).

The reaction of the oxo compounds of the formula I with the reducing agents is expediently carried out in a suitable solvent at temperatures between about $-100°$ C. and $+150°$, in particular between about $-10°$ and $0°$. Depending on the chemical nature of the reducing agent, suitable solvents are, for example, water, alcohols such as methanol, ethanol, isopropanol or butanol, ethers such as tetrahydrofuran, dioxane, diethyl ether or ethylene glycol dimethyl ether and hydrocarbons such as pentane, cyclohexane, benzene or toluene.

Above and below, $R^1$, $R^2$, $R^3$, $R^4$, $R^9$, $R^{10}$, X, Y, Z and n have the meaning indicated, if not expressly stated otherwise.

The radical $R^1$ is preferably a radical of the formula $R^3R^4CH$ or $SiR^5R^6R^7$. In these, the radicals $R^3$ and $R^4$ are preferably H, $C_1-C_4$-alkyl, or phenyl or benzyl which are unsubstituted or monosubstituted or polysubstituted by $C_1-C_3$-alkyl and/or alkoxy; $R^3$=H and $R^4$=phenyl at the same time are particularly preferred.

The radicals $R^5$, $R^6$ and $R^7$ are preferably $C_1-C_4$-alkyl or phenyl which is unsubstituted or substituted by $C_1-C_3$ (lacuna); particularly preferably $R^5$ and $R^6$ are at the same time methyl or phenyl and $R^7$ is methyl or tert.-butyl.

$R^2$ is preferably a protective group for the nitrogen atom linked to it, which makes it possible to convert the compound of the formula I into a D-(+)-biotin derivative whose nitrogen atom is protected with $R^2$, using the process according to the invention, and then to remove this protective group selectively under mild conditions.

Protective groups of this type are familiar to the person skilled in the art (for example Protective Groups in Organic Chemistry, Plenum Press, New York, 1973) and can be introduced and removed by known methods. Preferred $R^2$ radicals are, for example, benzyl, methoxybenzyl, 3,4-dimethoxybenzyl, 4-methylbenzyl, allyl, methallyl, crotyl, trimethylsilyl or tert.-butyldimethylsilyl, diphenylmethyl, trityl, 9-H-fluorenyl, 9-phenyl-9-fluorenyl or methoxymethyl.

X is O or S, preferably O.

The alcohol of the formula II is reacted with an electrophile of the formula III in an inert solvent in the presence of a base, the alkylation products of the formula IV being obtained by alkylation of the sulfhydryl group. In the alkylating agent of the formula III, Y is a leaving group, preferably a halogen such as Cl, Br or I, or a sulfonic acid radical —O—SO$_2$—R'', in which R'' is preferably p-toluyl, methyl or trifluoromethyl. Y is particularly preferably Cl or bromine. In the compounds of the formulae III, IV, IVa and V, Z is preferably O or N—R', in which R' is an alkyl group or a dialkylamino group. If Z is N—R', the corresponding ketones (Z=O) are obtained by hydrolysis of the appropriate imines or hydrazones in a manner known per se.

In the compounds of the formulae III, IV, IVa, V and VI, R$^9$ is preferably alkyl or alkenyl having up to 8 C atoms, —(CH$_2$)$_n$—CN, —(CH$_2$)$_n$—COOR or —(CH$_2$)$_n$—OR, in which R is lower alkyl and n is 2, 3, 4, 5, 6, 7 or 8. R$^9$ is preferably a radical which can be converted into a radical of the formula —(CH$_2$)$_3$—CO$_2$R in a manner known per se. R$^9$ is in particular n-butyl, 3-cyanopropyl, 3-(alkoxycarbonyl)propyl, 2-alkoxyethyl, 3-alkoxypropyl or 4-alkoxybutyl, alkoxy preferably being methoxy, ethoxy, n-propoxy or i-propoxy. The compounds of the formula II are alkylated with the electrophiles of the formula III in the presence of a base.

Suitable bases for this purpose are, for example, alkali metal hydroxides such as sodium hydroxide or potassium hydroxide, alkali metal carbonates such as sodium hydrogencarbonate, potassium carbonate or potassium hydrogencarbonate, alkali metal acetates such as sodium acetate or potassium acetate, alkaline earth metal hydroxides and oxides such as calcium hydroxide, calcium oxide or aluminum oxide or organic bases such as triethylamine, diisopropylethylamine, pyridine, lutidine, piperidine, morpholine, piperazine, collidine, quinoline or N,N-dimethylaminopyridine, in particular triethylamine or pyridine. The reaction is expediently carried out in an inert solvent. Suitable inert solvents are preferably hydrocarbons such as cyclohexane, benzene or toluene, ethers such as tetrahydrofuran or dioxane, amides such as dimethylformamide or hexamethylphosphoric triamide, sulfoxides such as dimethyl sulfoxide, alcohols such as methanol or ethanol or esters such as ethyl acetate. An excess of organic base is also suitable as a solvent.

The reaction temperatures are expediently between about 0° and 200° C., preferably between 20° and 150° C., and the reaction times are between about 1 and 48 hours.

The alkylation products of the formula IV are preferably etherified to give the ethers of the formula IVa. In the ethers of the formula IVa, R$^{10}$ is preferably methyl, ethyl, n-propyl, n-butyl, n-pentyl, n-hexyl, trimethylsilyl, triisopropylsilyl or tert.butyldimethylsilyl and furthermore i-propyl and tert.butyl.

The alkyl ethers of the formula IVa (R$^{10}$=C$_1$-C$_6$-alkyl) can be prepared by the methods known and utilizable for etherifications, such as are described, for example, in Houben-Weyl, Methoden der Organischen Chemie (Methods of Organic Chemistry), Vol. 6/3, p. 1 et seq. Preferably, the appropriate alcohols of the formula R$^{10}$—OH are reacted with the alcohol of the formula IV with the addition of a catalytic amount of acid or of a dehydrating agent such as, for example, an acid such as sulfuric acid, phosphoric acid, hydrogen chloride or p-toluenesulfonic acid, an acid derivative such as phosphorus pentoxide, phosphorus trichloride or phosphorus oxychloride, an acidic ion exchanger or molecular sieves.

The etherification is carried out in a suitable solvent, the pure alcohol R$^{10}$—OH or a mixture of a suitable solvent and the alcohol R$^{10}$—OH.

Suitable solvents are, for example, benzene, toluene, chloroform, dichloroethane, diethyl ether and tetrahydrofuran. The etherification is preferably carried out at temperatures between −20° C. and +150° C. Particularly preferably, the etherification is carried out in weakly acidic medium, i.e. at a pH between 2 and 4, preferably between 2.5 and 3.5, in order to suppress dehydration of the alcohol of the formula IV.

The trialkylsilyl enol ethers are prepared by reaction of the alcohols of the formula IV or of the ethers of the formula IVa, if appropriate after conversion of the group Z which is different from O (Z=S, N—R') into O, using a silylating reagent in the presence of a base in an inert solvent.

Suitable silylating reagents are the trialkylsilyl halides such as, for example, trimethylchlorosilane (TMCS), triisopropylchlorosilane (TIPCS), tert.butyldimethylchlorosilane (TBDMCS), trimethylbromosilane (TMBS) and trimethyliodosilane (TMIS), trialkylsilyl triflates such as, for example, trimethylsilyl triflate (TMSOTf), thexyldimeetthylsilyl (sic) triflate (ThDMSOTf) and triisopropylsilyl triflate (TIPSOTf) and ethyl trimethylsilyl acetate (ETSA), N,O-bis(trimethylsilyl)acetamide (BSA), N-methyl-N-trimethylsilyltrifluoroacetamide (MSTFA) and hexamethyldisilazane (HMDS).

The trialkylsilyl triflates are particularly preferred, as these allow carrying out of the reaction under kinetic control at temperatures between −60° and 10° C., preferably between −30 and 0° C. At these temperatures, the reactions are usually complete after 10 minutes to 48 hours.

Organic amines are suitable as bases. Suitable organic amines are, for example, pyridine, triethylamine, diisopropylamine, piperidine, morpholine, tert. butylamine, collidine, quinoline, 4-N,N-dimethylaminopyridine, diisopropylethylamine, 1,8-diazabicyclo[5.4.0]undec-7-ene (DBU) and 1,6-diazabicyclo[4.3.0]non-5-ene (DBN).

The silyl enol ether thus obtained of the formula IVb

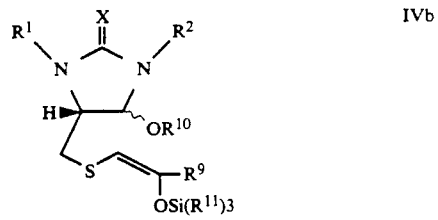

in which R$^1$, R$^2$, R$^9$, R$^{10}$ and X have the meaning indicated, and R$^{11}$ in each case independently of one another is an alkyl group having 1-6 C atoms, is cyclized in situ by means of a Lewis acid to give a biotin derivative of the formula V.

Suitable Lewis acids are aluminum, tin, zinc and titanium halides or triflates, such as, for example, aluminum chloride, tin tetrachloride, zinc chloride and titanium tetrachloride, boron halides and esters of boric acid, such as, for example, boron trifluoride, boron trichloride and trimethyl borate or trialkylsilyl triflates such as, for example, trimethylsilyl triflate and triisopropylsilyl triflate.

The reaction temperature is usually between −90° C. and 0° C., preferably between −90° and −50° C. At these temperatures, the reactions are usually complete after 15 minutes to 4 hours.

In a preferred embodiment of the process according to the invention, the alcohol of the formula IV or the ether of the formula IVa is converted into the silyl enol ether of the formula IVb using about one equivalent of trialkylsilyl triflate in an inert solvent in the presence of a base at a temperature between −30° C. and 0° C. and, after cooling to a temperature between 90° C. (sic) and −50° C., cyclized in situ to the biotin derivative of the formula V by addition of a further sub-stoichiometric amount of the same trialkylsilyl triflate. The biotin derivative of the formula V is present as a mixture of the diastereomers of the formulae Va and Vb.

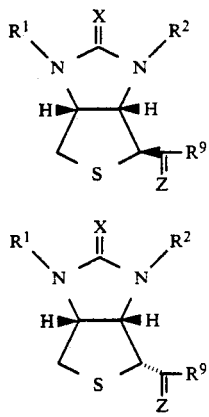

The ratio of these diastereomers can be influenced by suitable carrying out of the reaction.

In particular, higher proportions of the diastereomer of the formula Vb are obtained by conversion of the alcohol of the formula IV or of the ether of the formula IVa into the silyl enol ether of the formula IVb at low temperatures using trialkylsilyl triflates and cyclization.

The biotin derivatives of the formula Vb can be reduced to biotin derivatives of the formula VIII,

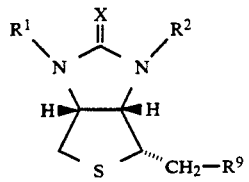

in which $R^1$, $R^2$, $R^9$ and X have the meaning indicated, using suitable reducing agents. These biotin derivatives of the formula VIII are known and can be reacted by methods known per se, as disclosed, for example, in DE-2,058,234, EP-0,036,030, EP-0,084,377 and U.S. Pat. No. 3,859,167, to give D-(+)-biotin.

Suitable reducing agents for the reduction of the biotin derivatives of the formula Vb to those of the formula VIII are, for example, zinc amalgam in aqueous hydrochloric acid (Clemmensen reduction), hydrazine hydrate in the presence of bases (Wolff-Kishner or Huang-Minlon reduction), hydrogen in the presence of hydrogenation catalysts at 180° to 250° C. or by conversion of the keto group (Z=O) into the corresponding tosylhydrazone (Z=N—NH—SO$_2$—C$_7$H$_7$) and also complex hydrides such as, for example, lithium aluminohydride or sodium borohydride.

The diastereomer mixture of the formulae Va and Vb can furthermore be converted by reduction to the alcohol of the formula Vc

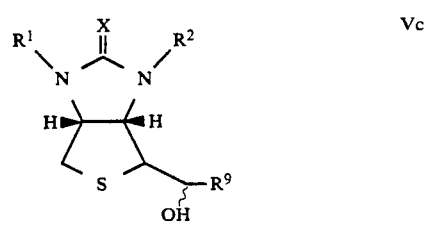

in which $R^1$, $R^2$, $R^9$ and X have the meaning indicated, using a complex reducing agent and subsequent dehydration, to give a dehydrobiotin derivative of the formula VI. Suitable complex reducing agents are in particular those which are also used for the reduction of the cysteine hydantoins in the formula I.

The reaction of the complex hydrides with the compounds of the formula V is advantageously carried out in an inert solvent, a protic solvent or a mixture of an inert and a protic solvent. Suitable inert solvents are preferably hydrocarbons such as pentane, hexane, cyclohexane, benzene or toluene, ethers such as diethyl ether, tetrahydrofuran, dioxane or ethylene glycol dimethyl ether and mixtures of these solvents with one another. Suitable protic solvents are preferably alcohols such as methanol, ethanol, isopropanol and butanol. The reaction temperatures are expediently between about −120° C. and +150° C., preferably between −80° C. and +100° C., and the reaction times are between about 30 minutes and 24 hours.

Acids such as sulfuric acid, hydrochloric acid, phosphoric acid, toluenesulfonic acid or bases such as sodium hydroxide or potassium hydroxide, for example, are suitable for the dehydration of the alcohols of the formula Va. The reaction can in this case be carried out in the presence or absence of an inert solvent at temperatures between about 0° C. and 150° C., preferably between 20° C. and 100° C. Suitable solvents are, for example, alcohols such as methanol, ethanol, isopropanol or butanol. The alcohols of the formula Vc are preferably converted into the corresponding mesylate using mesyl chloride and subsequently heated in the presence of a base.

The dehydrobiotin derivatives of the formula VI are known and can be reacted to give D-(+)-biotin by methods known per se (for example EP 0,084,377).

The process according to the invention thus allows the preparation of optically active D-(+)-biotin in a simple and stereospecific manner and in high yields from easily accessible, inexpensive starting materials in a few synthesis steps, which can in some cases be carried out in a one-pot process, and thus represents a substantial advance in the area of biotin synthesis.

The following examples are intended to illustrate the process according to the invention in more detail without limiting it. The following abbreviations are used:

| TBAF | Tetrabutylammonium fluoride |
| THF | Tetrahydrofuran |
| DIBAH | Diisobutylaluminum hydride |
| ETOAC | Ethyl acetate |
| TEA | Triethylamine |
| TMSOTf | Trimethylsilyl triflate |
| TIPSOTf | Triisopropylsilyl triflate |
| DBU | Diazabicyclo[5.4.0]undec-7-ene |
| ETSA | Ethyl trimethylsilyl acetate |

The specific rotations are measured on a Perkin-Elmer polarimeter in the solvent indicated in each case.

The column chromatographic separations are carried out on silica 60 230–400 mesh.

EXAMPLE 1

A solution of 324.4 g (1.0 mol) of (7aR)-3-phenyl-6-benzyl-1H,3H-imidazo[1,5-c]thiazole-5,7-dione in 3200 ml of anhydrous acetic acid is treated with 261.6 g (4.0 mol) of zinc powder in portions at 85° C., and the mixture is stirred at 85° C. for a further 6 hours, filtered and concentrated under reduced pressure.

The residue is dissolved in 1000 ml of toluene, and the solution is washed successively with 300 ml of 1N hydrochloric acid and 400 ml of water, dried over sodium sulfate and concentrated under reduced pressure.

308.5 g of N,N'-dibenzyl-L-cysteine hydantoin are obtained as a colorless oil.

$[\alpha]_{365}^{20} = -190°$, c=1 (methanol).

EXAMPLE 2

A mixture of 9.8 g (30 mmol) of N,N'-dibenzyl-L-cysteine hydantoin (prepared according to Example 1) and 200 ml of THF is treated with 66 ml of a solution of DIBAH in THF (1 mol/1) at −70° C. After stirring at −70° C. for one hour, 50 ml of water and 200 ml of a 2.5% aqueous sodium hydroxide solution are successively added dropwise.

After stirring at room temperature for one hour, the phases are separated and, after customary working-up and chromatographic purification (ETOAc/hexane 1:1), 9.82 g (99% of theory) of (4 RS, 5 R)-1,3-dibenzyl-2-oxo-5-mercaptomethylimidazolidin-4-ol, $R_f$=0.40 (EtOAc/hexane 1:1) are obtained.

$[\alpha]_D = -14.8°$, c=0.870 (CHCl$_3$).

EXAMPLE 3

A mixture of 1.85 g (5.63 mmol) of (4 RS, 5 R) 1,3-dibenzyl-2-oxo-5-mercaptomethylimidazolidin-4-ol (prepared according to Example 2) and 7.0 ml of THF is treated at 0°-5° C. with 0.855 g (1.18 ml, 8.45 mmol) of TEA and 0.547 g (0.47 ml, 5.91 mmol) of chloroacetone. The mixture is stirred at 0° C. for 2 hours and then at room temperature for 2 hours. The precipitate is filtered off and the solvent is removed by distillation. After flash chromatography, 1.956 g (90% of theory) of (4 RS, 5 R)-1,3-dibenzyl-2-oxo-5-(4-oxo-2-thiapentyl)imidazolidin-4-ol, $R_f$=0.24 (EtOAc/hexane 3:2) are obtained.

The following are prepared analogously:

(4 RS, 5 R)-1,3-dibenzyl-2-oxo-5-(4-oxo-4-phenyl-2-thiabutyl)imidazolidin-4-ol, yield: 88% of theory, $R_f$=0.44 (EtOAc/hexane 1:1).

(4 RS/5 R)-1,3-dibenzyl-2-oxo-5-(4-oxo-7-(methoxycarbonyl)-2-thiaheptyl)imidazolidin-4-ol, yield 85% of theory, $R_f$=0.41 (EtOAc/hexane 3:2).

$[\alpha]_D = +34.8°$, c=1.150 (CHCl$_3$).

EXAMPLE 4

A mixture of 2.12 g (4 RS, 5 R)-1,3-dibenzyl-2-oxo-5-(4-oxo-4-phenyl-2-thiabutyl)imidazolidin-4-ol (prepared according to Example 3) and 100 ml of ethanol is brought to pH 3.1 (against Methyl Orange) at 0°-5° C. using 2 normal sulfuric acid in ethanol. After stirring at 0°-5° C. for two hours, the mixture is brought to pH 5 to 6 using 2% potassium hydroxide in ethanol. After customary working-up and flash chromatography, 2.043 g (91% of theory) of (4 RS, 5 R)-1,3-dibenzyl-2-oxo-5-(4-oxo-4-phenyl-2-thiabutyl)-4-ethoxyimidazolidine, $R_f$=0.69 (EtOAc/hexane 3:7), are obtained. The following are oxo-7-(methoxycarbonyl)-2-thiaheptyl)-4-ethoxyimidazolidine, yield 85% of theory, $R_f$=0.62 (EtOAc/hexane 1:1), (4 RS, 5 R)-1,3-dibenzyl-2-oxo-4-ethoxy-5-mercaptomethylimidazolidine, yield 80% of theory.

$[\alpha]_D^{20} = +20.1°$, c=1 (methanol).

(4 RS, 5 R)-1,3-dibenzyl-2-oxo-4-ethoxy-5-(4-oxo-2-thiapentyl)imidazolidine.

EXAMPLE 5

Under a nitrogen atmosphere, 328 mg of TEA are added dropwise at −20° C. to a mixture of 761 mg of (4 RS, 5 R)-1,3-dibenzyl-2-oxo-5-(4-oxo-7-(methoxycarbonyl)-2-thiaheptyl)imidazolidin-4-ol (prepared according to Example 3) and 10 ml of dry dichloromethane. A mixture of 722 mg of TMSOTf and 2 ml of dry dichloromethane are added dropwise to this reaction mixture. After warming to room temperature, the mixture is additionally stirred for a further 1.5 hours. After cooling to −60° C., a mixture of 180 mg of TMSOTf and 1 ml of dry dichloromethane is added dropwise.

After half an hour, the reaction mixture is poured into an aqueous sodium hydrogencarbonate solution and extracted using dichloromethane. The organic phases are dried over potassium carbonate and evaporated. After column chromatography and recrystallization, 305 mg (42% of theory) of (3aS, 4S, 6aR)-1,3-dibenzyl-4-(1-oxo-4-methoxycarbonylbutyl)tetrahydrothieno[3,4-d]imidazolidin-(3H)one (cyclization product) having a melting point of 80°-81° C. are obtained.

$[\alpha]_D^{20} = -15.6°$, c=0.58 (CHCl$_3$), $R_f$=0.42 (EtOAc/hexane 1:1 + 1% TEA).

In addition, 293 mg (40% of theory) of 1,3-dibenzyl-2-oxo-4-(4-oxo-7-methoxycarbonyl-2-thiaheptyl)-imidazolidin-4-ene (elimination product) are obtained as a by-product $R_f$=0.25 (EtOAc/hexane 1:1 + 1% TEA).

EXAMPLE 6

384 mg of (4 RS, 5 R)-1,3-dibenzyl-2-oxo-5-(4-oxo-2-thiapentyl)imidazolidin-4-ol in 2 ml of dichloromethane is (sic) cooled to −20° C. and treated with 212 mg of triethylamine and 456 mg of TMSOTf. After stirring at room temperature for 1½ h, the solution is cooled to −70° C. 222 mg of TMSOTf are added and the mixture is stirred at −70° for a further 1 h. The mixture is poured into aq. NaHCO$_3$ and the organic phase is dried over K$_2$CO$_3$. After removal of the solvent, the residue is separated using flash chromatography. 108 mg (30% of theory) of (3aS, 4S, 6aR)-1,3-dibenzyl-4-acetyltetrahydrothieno[3,4d]imidazolidin-2(3H)one are obtained, melting point: 119$^5$-121$^5$ (sic) ° C., $R_f$=0.61 (EtOAc/hexane 1:1).

$[\alpha]_D = 59.2°$, c=1.195, (CHCl$_3$).

EXAMPLE 7

In analogy to the reaction described previously, 223 mg of (4 RS, 5 R)-1,3-dibenzyl-2-oxo-5-(4-oxo-4-phenyl-2-thiabutyl)imidazolidin-4-ol in dichloromethane (2 ml) are reacted with 160 mg of diazabicyclo[5.4.0]undec-7-ene (DBU), 160 mg of TMSOTf at −20° C. and a further 56 mg of TMSOTf. After working-up, 98 mg (46%) of (3aS, 4S, 6aR)-1,3-dibenzyl-4-benzoyltetrahydrothieno[3,4-d]-imidazolidin-2(3H)one, $R_f$=0.60 (EtOAc/hexane 1:1), are obtained. Melting point: 127–128$^5$ (sic) ° C.

$[\alpha]_D$= +91.2°, c=1.04, (CHCl$_3$).

EXAMPLE 8

A mixture of 237 mg of (4 RS, 5 R)-1,3-dibenzyl-2-oxo-5-(4-oxo-4-phenyl-2-thiabutyl)-4-ethoxyimidazolidine (prepared according to Example 4) and 2 ml of dichloromethane is treated with 53 mg of TEA and 111 mg of TMSOTf at −20° C. analogously to Example 7 and the mixture is stirred at room temperature for 1.5 hours, and a further 111 mg of TMSOTf are then added at −60° C. 165 mg (77% of theory) of (3aS, 6aR, 4R)-1,3-dibenzyl-4-benzoyltetrahydrothieno[3,4 d]imidazolidin-2(3H)one, $R_f$=0.51 (EtOAc/hexane 3:2) are obtained having a melting point of 143°–144° C.

$[\alpha]_D$= −77.6°, c=1.135 (CHCl$_3$).

The following is obtained analogously from (4 RS, 5 R)-1,3-dibenzyl-2-oxo-4-ethoxy-5-(4-oxo-2-thiapentyl-)imidazolidine (prepared according to Example 4)

(3aS, 6aR, 4R)-1,3-dibenzyl-4-acetyltetrahydrothieno[3,4 d]imidazolidin-2(3H)one

EXAMPLE 9

A mixture of 500 mg of (4 RS, 5 R)-1,3-dibenzyl-2-oxo-5-(4-oxo-7-(methoxycarbonyl)-2-thiaheptyl)-4-ethoxyimidazolidine (prepared according to Example 4) and 4 ml of dichloromethane is reacted with 111 mg of TEA and a total of 467 mg of TMSOTf analogously to Example 5. In (sic) 310 mg (69% of theory) of a 1:1 diastereomer mixture of (3aS, 6aR, 4S)- and (3aS, 6aR, 4R)-1,3-dibenzyl-4-(1-oxo-4-methoxycarbonylbutyl)tetrahydrothieno[3,4d]imidazolidin-2(3H)one are obtained, $R_f$=0.65 (EtOAc/hexane=3:2).

EXAMPLE 10

A mixture of 500 mg of (4 RS, 5 R)-1,3-dibenzyl-2-oxo-5-(4-oxo-7-(methoxycarbonyl)-2-thiaheptyl)-4-ethoxyimidazolidine (prepared according to Example 4) and 4 ml of dichloromethane is stirred at −20° C. and (sic) 111 mg of TEA and 222 mg of TMSOTf for 10 hours. After cooling to −60° C., addition of a further 245 mg of TMSOTf and stirring for a further half an hour, 310 mg (69% of theory) of a 2:1 diastereomer mixture of (3aS, 6aR, 4R)- and (3aS, 6aR, 4S)-1,3-dibenzyl-4-(1-oxo-4-methoxycarbonylbutyl)tetrahydrothieno[ 3,4d]imidazolidine-2(3H)-one are obtained. The pure (3aS, 6aR, 4R)-diastereomer having a melting point of 101°–102° C. is obtained by recrystallization.

$[\alpha]_D$= −10.7°, c=0.205 (CHCl$_3$).

Using tosylhydrazine, this is converted into the corresponding tosylhydrazone, which is reduced with sodium borohydride. (3aS, 6aR, 4R)-1,3-dibenzyl-4-(4-methoxycarbonylbutyl)tetrahydrothieno[3,4-d]imidazolidin-2(3H)one (dibenzylbiotin methyl ester) is obtained.

EXAMPLE 11

A mixture of 452.6 mg of (3aS, 6aR)-1,3-dibenzyl-4-(1-oxo-4-methoxycarbonylbutyl)tetrahydrothieno[3,4-d]imidazolidin-2(3H)one (1:1 (4 RS)-diastereomer mixture, prepared according to Example 9) and 40 ml of methanol is treated with 38 mg of sodium borohydride at room temperature and the mixture is stirred for 60 minutes. It is then concentrated under reduced pressure, the residue is taken up in 40 ml of water and the solution is extracted twice using 30 ml of diethyl ether each time. The combined organic phases are dried over sodium sulfate and concentrated under reduced pressure.

(3aS, 6aR)-1,3-dibenzyl-4-(1-hydroxy-4-methoxycarbonylbutyl)tetrahydrothieno[3,4-d]imidazolidin-2(3H)-one is obtained as a residue.

The crude product is then dissolved in a mixture of 15 ml of dichloromethane and 15 ml of triethylamine and the solution is treated at room temperature with 573 mg of methanesulfonyl chloride (mesyl chloride). The solution is stirred at 35° C. for 90 minutes, filtered and concentrated under reduced pressure.

The crude mesylate is then dissolved in 15 ml of DBU and stirred at 60° C. for 2 hours. The reaction mixture is then cooled to room temperature, diluted with 75 ml of toluene and washed successively with 30 ml each of 2N hydrochloric acid and water.

The mixture is dried over sodium sulfate and concentrated under reduced pressure, and the residue is chromatographed on silica gel (diethyl ether).

388 mg of (3aS, 6aR)-1,3-dibenzyl-4-(4-methoxycarbonylbutylidene)tetrahydrothieno[3,4-d]imidazolidin-2(3H)one are obtained.

$[\alpha]_D^{22}$= +227°, c=1 (benzene).

By hydrolyzing in alcoholic potassium hydroxide solution, this is converted into the corresponding carboxylic acid, melting point 81°–83° C.

$[\alpha]_D^{22}$: +217°, c=1 (methanol) which is converted into D-(+)-biotin according to EP-0,084,377.

EXAMPLE 12

Under a nitrogen atmosphere, 168 mg of ETSA are added dropwise at −70° C. to a mixture of 249 mg of (4RS, 5R)-1,3-dibenzyl-2-oxo-5-(4-oxo-7-(methoxycarbonyl)-2-thiaheptyl-4-ethoxyimidazoline (prepared according to Example 4) and 1 ml of dry tetrahydrofuran. A catalytic amount of TBAF in dry tetrahydrofuran is added dropwise to this reaction mixture. After warming to room temperature, the mixture is additionally stirred for a further 24 hours and concentrated under reduced pressure.

The residue is dissolved in 2 ml of dichloromethane. After cooling to −70° C., a mixture of 165 mg of TMSOTf and 1 ml of dichloromethane is added dropwise.

After stirring at −70° C. for one hour and additional working-up, 176 mg (78% of theory) of a 3:2 diastereomer mixture of (3αS, 6αR, 4R)- and (3αS, 6αR, 4S)-1,3-dibenzyl-4-(1-oxo-4-methoxycarbonylbutyl)tetrahydrothieno[3,4,d]imidazolidin-2(3H)one are obtained. (Cyclization product).

In addition, 33 mg (7% of theory) of 1,3-dibenzyl-2-oxo-4-(4-oxo-7-(methoxycarbonyl)-2-thiaheptyl-)imidazolidin-4-ene are obtained as by-product. (Elimination product).

We claim:

1. A compound of formula II,

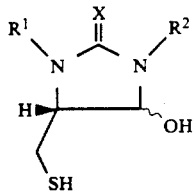

wherein

R¹ is H, or a group R³R⁴CH— or —SiR⁵R⁶R⁷, in which

R³ and R⁴ are each independently H, unsubstituted alkyl, cycloalkyl or unsubstituted or C₁₋₃-alkyl-monosubstituted aryl, aralkyl or, taken together, are unsubstituted alkylene;

R⁵ and R⁶ and R⁷ in each case independently of one another are unsubstituted alkyl, cycloalkyl, aryl or R² is H or a protective group suitable for a nitrogen atom; and X is O, S or N—R⁸, in which R⁸ is an alkyl, cycloalkyl, aryl or alkoxycarbonyl group or a dialkylamino group.

2. A compound according to claim 1, wherein R³ and R⁴ are each independently H, C₁₋₄-alkyl, or phenyl or benzyl which are unsubstituted or monosubstituted by C₁₋₃-alkyl.

3. A compound according to claim 2 wherein R³ is H and R⁴ is phenyl.

4. A compound according to claim 1 wherein R⁵, R⁶ and R⁷ are each independently C₁₋₄-alkyl or phenyl.

5. A compound according to claim 4 wherein R⁵ and R⁶ are at the same time methyl or phenyl or R⁷ is methyl or tert-butyl.

6. A compound according to claim 1 wherein R² is benzyl, methoxybenzyl, 3,4-dimethoxybenzyl, 4-methylbenzyl, allyl, methally, crotyl, trimethylsilyl, tert-butyldimethylsilyl, diphenylmethyl, trityl, 9-H-fluorenyl, 9-phenyl-9-fluorenyl or methoxymethyl.

7. A compound according to claim 1 wherein X is O.

8. Compound according to claim 1, characterized in that R¹ and R² are benzyl.

* * * * *